United States Patent [19]

Zhang et al.

[11] Patent Number: 5,672,798

[45] Date of Patent: *Sep. 30, 1997

[54] FLUIDIZED BED SOLID CATALYST MOTOR FUEL ALKYLATION PROCESS

[75] Inventors: Scott Yu-Feng Zhang, Carol Stream; Christopher David Gosling, Roselle; Paul Alvin Sechrist, Des Plaines; Gregory A. Funk, Carol Stream, all of Ill.

[73] Assignee: UOP, Des Plaines, Ill.

[*] Notice: The term of this patent shall not extend beyond the expiration date of Pat. No. 5,489,732.

[21] Appl. No.: 597,048

[22] Filed: Feb. 5, 1996

Related U.S. Application Data

[63] Continuation-in-part of Ser. No. 323,437, Oct. 14, 1994, Pat. No. 5,489,732.

[51] Int. Cl.[6] .................. C07C 2/68; C07C 2/56; C07C 2/58
[52] U.S. Cl. .................. 585/467; 585/710; 585/721; 585/722; 502/31; 502/53
[58] Field of Search .................. 585/710, 721, 585/467, 722; 502/31, 53

[56] References Cited

U.S. PATENT DOCUMENTS

| | | | |
|---|---|---|---|
| 3,851,004 | 11/1974 | Yang | 260/671 C |
| 4,008,291 | 2/1977 | Zabransky et al. | 260/683.43 |
| 4,028,430 | 6/1977 | Stine et al. | 260/683.43 |
| 4,139,573 | 2/1979 | Carson | 260/683.49 |
| 4,973,780 | 11/1990 | Johnson et al. | 585/467 |
| 5,157,196 | 10/1992 | Crossland et al. | 585/720 |

*Primary Examiner*—Glenn A. Caldarola
*Assistant Examiner*—Thuan D. Dang
*Attorney, Agent, or Firm*—Thomas K. McBride; John F. Spears, Jr.

[57] ABSTRACT

Hydrocarbons are alkylated in a fluidized riser-reactor using a solid catalyst which is regenerated within the process by contact with hydrogen. The alkylation and regeneration steps are separated to prevent the admixture of hydrogen and any olefins present in the process. Two separate modes of regeneration are performed simultaneously: a mild liquid-phase washing and a vapor-phase hot hydrogen stripping operation.

10 Claims, 2 Drawing Sheets

5,672,798

FLUIDIZED BED SOLID CATALYST MOTOR FUEL ALKYLATION PROCESS

CROSS REFERENCE TO RELATED APPLICATION

This application is a continuation-in-part of prior application 08/323,437 filed 14 Oct. 1994 and now U.S. Pat. No. 5,489,732.

BACKGROUND OF THE INVENTION

FIELD OF THE INVENTION

The invention relates to a hydrocarbon conversion process. The invention specifically relates to the alkylation of hydrocarbons such as aromatics or paraffins to produce useful chemicals and motor fuel. The invention is primarily directed to a process for the solid bed alkylation of isobutane to produce $C_8$ isoparaffins useful as motor fuel blending components.

RELATED ART

Large amounts of high octane gasoline are produced by the alkylation of isobutane with butenes. Likewise, large amounts of valuable aromatic hydrocarbons including cumene, ethylbenzene and $C_{16}$–$C_{21}$ linear alkylaromatics are produced by the alkylation of benzene with olefins of the appropriate carbon number. The variety of feed reactants and the passage of time has led to the development of a number of effective alkylation technologies which are employed in large scale commercial facilities.

One of the most widely used processes for the production of motor fuel is HF alkylation as described in U.S. Pat. No. 4,139,573 issued to D. B. Carson, which provides an overview of the HF alkylation process. One of the advantages of the use of liquid-phase HF as a catalyst is its resistance to deactivation, and the relative ease with which a slipstream may be removed from an onstream reaction zone for "regeneration". The HF itself is not chemically changed during use but various organic reaction by-products such as "acid soluble oils" (ASO) accumulate in the liquid-phase HF and are removed during this regeneration.

Regeneration is also necessary for all solid bed motor fuel alkylation catalysts developed to date since they tend to suffer from a high deactivation rate. Deactivation of solid catalysts is due to different, possibly multiple, causes from those encountered with liquid HF as a catalyst and usually includes some accumulation of hydrocarbonaceous deposits on the catalyst.

A common method of regenerating catalysts is by combustion of organic deposits. This is often not desired for alkylation catalysts. U.S. Pat. No. 3,851,004 to C. L. Yang describes an alternative method for regenerating a solid bed alkylation catalyst comprising a hydrogenation component on a zeolitic support which comprises contacting the catalyst with a hydrogen-containing liquid-phase saturated hydrocarbon.

Any interruption in the operation of the reaction zone to regenerate or replace catalyst is undesirable. Certain operating benefits are provided to any process by an ability to operate in a continuous manner, which makes it desirable to find a means to regenerate or replace the catalyst while the reaction zone is kept in use. U.S. Pat. No. 4,973,780 issued to R. C. Johnson et al describes a moving bed benzene alkylation process in which catalyst is continuously or periodically replaced with regenerated catalyst to provide countercurrent catalyst-reactant flows. Cocurrent flow with catalyst added to the bottom of the reactor is also disclosed.

It has also been proposed to provide continuous operation by simulating the movement of the catalyst through the reaction and regeneration zones. U.S. Pat. Nos. 4,008,291 to R. F. Zabransky et al. and 4,028,430 to L. O. Stine et al. describe the use of simulated countercurrent operations to perform a number of alkylation reactions including the production of motor fuel. These references provide separate reaction and catalyst reactivation zones, with an external regenerant stream being employed for the reactivation. In both references the effluent of the reaction zone is withdrawn from the alkylation zone immediately upon its exit from the reaction zone. These references also teach the use of a "pump around" stream to complete the simulation and provide a continuous liquid loop.

Finally, U.S. Pat. No. 5,157,196 issued to C. S. Crossland et al. describes a moving bed paraffin alkylation process which employs a plug flow in which the catalyst moves upward to a disengaging zone. Used catalyst from the disengaging zone is passed into a wash zone.

BRIEF SUMMARY OF THE INVENTION

The invention is a fluidized process for the alkylation of hydrocarbons. The invention provides a continuous reaction zone which is not interrupted for the periodic regeneration of catalyst. The invention also eliminates the need to perform motor fuel alkylation reactions using volatile and hazardous liquid phase hydrofluoric acid. The invention is characterized by the use of a fluidized riser-type reaction zone with the upper end of the reaction zone discharging into a separate zone in which the reactants and products are separated from used catalyst and the used catalyst is then stripped and recirculated to the riser. A first portion of the used catalyst is mildly regenerated while a second portion is drawn off for full regeneration in an external fluidized regeneration zone.

One broad embodiment of the invention may be characterized as a process for the alkylation of a feed hydrocarbon which comprises the steps of passing a first catalyst stream, comprising regenerated catalyst, and a feed stream comprising the feed hydrocarbon and an alkylating agent into the bottom of a vertical riser-reaction zone maintained at reaction conditions and producing a reaction zone effluent stream comprising used catalyst, the feed hydrocarbon and a product hydrocarbon; discharging the reaction zone effluent stream into a separation zone in which used catalyst is separated from liquid phase hydrocarbons and thereby forming a liquid-phase separation zone effluent stream comprising the feed and product hydrocarbons, with the thus separated used catalyst descending downward within the separation zone; transferring the used catalyst downward through a mild regeneration zone wherein the used catalyst is contacted with feed hydrocarbon containing dissolved hydrogen to form partially regenerated catalyst; transferring a portion of the used catalyst into a high temperature regeneration zone wherein the used catalyst is contacted with vapor phase hydrogen at vapor phase regeneration conditions to form regenerated catalyst, and withdrawing regenerated catalyst from the high temperature regeneration zone as a second catalyst stream; commingling the second catalyst stream with partially regenerated catalyst and employing at least a portion of the resulting admixture as the first stream of catalyst, which is admixed with the feed stream as per step (a); and recovering the product hydrocarbon from the separation zone effluent stream.

DETAILED DESCRIPTION AND PREFERRED EMBODIMENTS

Figure 1:
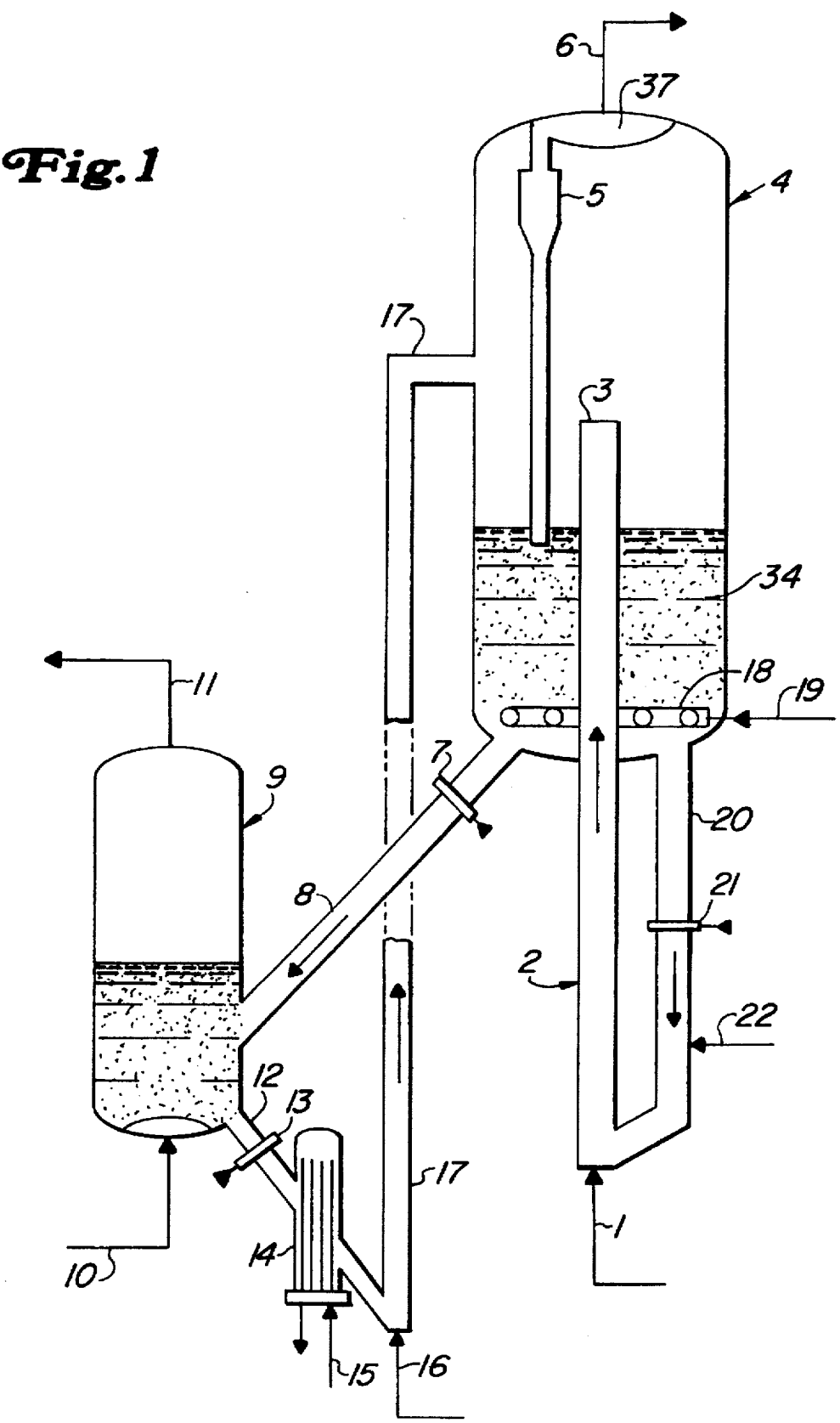
FIG. 1 is a simplified diagram illustrating an embodiment of the invention in which the riser-reactor 2 discharges into a large separation vessel 4, which retains a dense bed 34 of catalyst which is being subjected to mild liquid-phase regeneration.

Hydrocarbon alkylation is widely used in the petroleum refining and petrochemical industries to produce a variety of useful acyclic and cyclic hydrocarbon products which are consumed in motor fuel, plastics, detergent precursors, and petrochemical feedstocks. Much of the installed base of alkylation capacity uses liquid phase hydrofluoric acid, generally referred to as HF, as the catalyst. The use of HF in these applications has a long record of highly dependable and safe operation. However, the potential damage from an unintentional release of any sizeable quantity of HF and the need to safely dispose of some byproducts produced in the process has led to an increasing demand for alkylation process technology which does not employ liquid phase HF as the catalyst.

Numerous alkylation catalysts have been described in the open literature. However, those that we have knowledge of all appear to suffer from unacceptably high deactivation rates when employed at commercially feasible conditions. While some catalysts have a sufficiently useful lifetime to allow the performance of alkylation, the rapid change in activity results in a change in product composition and also requires the periodic regeneration of the catalyst with the accompanying removal of the reaction zone from operation. It is very desirable to provide a continuous process for alkylation which is not subjected to periodic reaction zone stoppages or variation in the product stream composition.

It is an objective of this invention to provide an alkylation process which does not employ liquid phase HF as the catalyst. It is a further objective of the subject invention to provide an alkylation process which utilizes a solid catalyst. It is a specific objective of the invention to provide a solid catalyst alkylation process for the production of motor fuel blending hydrocarbons. A further objective of the subject process is to provide a continuous process which delivers a uniform quality and quantity of product and which employs a solid alkylation catalyst.

The subject process achieves these objectives by the use of unique flow schemes in which a riser-type reactor delivers the product hydrocarbons and used catalyst to a liquid phase separation zone from which catalyst is removed for division between one of two regeneration zones.

The hydrocarbon feedstock to the subject process may be essentially any hydrocarbon which is retained as an easily flowable liquid phase material at the conditions employed in the reaction and mild regeneration zones and which may be alkylated via solid catalyst at the conditions maintained in the riser reaction zone. The feed hydrocarbon may therefore be an aromatic hydrocarbon such as benzene or toluene. This feed hydrocarbon or substrate is often reacted with an alkylating agent comprising an acyclic light olefin such as ethylene, propylene or butylene to produce such chemicals as ethylbenzene and cumene. A large amount of benzene is alkylated with higher carbon number olefins having from about 10 to about 15 carbon atoms per molecule to produce linear alkyl benzenes which are then sulfonated to produce detergents. For motor fuel production the preferred feed hydrocarbons are light paraffinic hydrocarbons such as the butanes. An especially preferred paraffinic feed hydrocarbon is isobutane.

The entering feed hydrocarbon is typically alkylated with a linear olefin having from 2 to about 15 carbon atoms per molecule. The feed hydrocarbon may also be reacted with an alkylating agent chosen from a variety of compounds other than olefins including monohydric alcohols. Examples of the alcohols which may be employed as the alkylating agent include ethanol and methanol. For instance, methanol is widely described in the literature as being useful in the paraselective methylation of benzene and toluene.

The operation of the subject invention may be best discerned by reference to the Drawing. In both figures, isobutane is the feed hydrocarbon and it is reacted with $C_4$ olefins to produce $C_8$ hydrocarbons which may be recovered by normal product recovery methods such as fractional distillation. Although there are differences between the two embodiments, the same numbering system has been employed on each one to the extent that the same or analogous equipment is employed.

As used herein the term "substantially free" means a molar concentration less than 1.5 mole percent. The term "rich" is intended to indicate a concentration of the specified compound or class of compounds greater than 50 mole percent.

Referring to FIG. 1, a liquid phase feed stream comprising an admixture of isobutane and $C_4$ olefins enters the process through line 1 at the bottom of the riser-reactor 2. The injection of this liquid results in the upward flow of the contents of the riser-reactor 2 including solid catalyst which travels downward through the transfer line 20 at a rate controlled by the slide valve 21. Liquid phase isobutane flows into the transfer line 20 through line 22 at a rate sufficient to cause a continuous minor net upward liquid flow through the conduit 20. This upward liquid flow is intended to strip hydrogen from the catalyst and surrounding liquid to prevent the entrance of hydrogen into the riser. Conduit 20 will therefore deliver a stream of hydrogen-free freshly regenerated catalyst to the bottom of the riser reactor. This catalyst is admixed with the entering reactant feed stream and catalyzes the reaction of olefins with the entering $C_4$ isobutane or recirculating isobutane to form $C_8$ product hydrocarbons. The reaction products, the residual isobutane and the now used catalyst exit from the top 3 of the riser reactor 2 and enter into a large volume cylindrical separation chamber 4. The flush stream of line 22 may be passed into the conduit above the slide valve 21, which may be preferable.

The low liquid velocities present within the separation vessel 4 allow the solid particulate catalyst to settle downward and form a dense fluid bed 34 located in a lower portion of the vessel. This bed is preferably maintained in a dense fluidized state by the passage of a liquid phase stream comprising isobutane and dissolved hydrogen into the vessel 4 through line 19. A distribution grid 18 is employed near the bottom of vessel 4 to achieve a uniform distribution of the entering liquid-phase isobutane containing dissolved hydrogen throughout the dense fluid bed. The catalyst retained within the fluid bed is therefore subjected to a mild regeneration procedure by contact with hydrogen saturated isobutane. This added isobutane of line 19 together with that from line 22 and the olefin-free liquid phase material exiting from the riser reactor 2 will gradually travel upward through the vessel 4 and enter into a cyclone type ("hydroclone") liquid-solids separator 5. The cyclone 5 effects the further separation of any entrained catalyst or catalyst fragments from the liquid phase hydrocarbons before the liquid is discharged into a plenum 37 at the top of the vessel 4. The plenum may be utilized to facilitate the installation of two or more separate cyclones into the separation vessel 4. The thus collected liquid phase hydrocarbons are removed from the process through line 6 as a product stream and transferred to the appropriate product recovery facilities not shown on the drawing.

The major portion of the used catalyst retained in the dense bed is withdrawn as a continuous stream through line 20 at the rate set by the slide valve 21. This first catalyst stream flows downward countercurrent to some of the hydrogen-free isobutane charged to the process via line 22. The remainder of this isobutane flows from line 22 into the riser 2. The purpose of this procedure is to prevent the entrance of hydrogen into the riser where it could saturate olefins added by line 1. If the catalyst employed in the process does not promote the hydrogenation of the olefins, then this washing procedure may be eliminated. Slide valve 21 will need to always be slightly open, or other means provided, to allow the flow of liquid upward through line 20 and ensure hydrogen does not enter the reactor 2. The hydrogen-free isobutane of line 21 can alternatively be passed into line 20 at a point above the slide valve 21.

A second and smaller stream of the catalyst present in the dense fluid bed at the bottom of the separation vessel 4 is withdrawn through line 8 at a flow rate controlled by the slide valve 7. This smaller stream comprises both solid catalyst and liquid-phase hydrocarbons and is passed into an external regeneration vessel 9, with the catalyst being retained in the regeneration vessel 9 for some average time set by the transfer rate in line 8. It is currently preferred that the second catalyst stream has a uniform flow rate but a variable rate could be used to facilitate batch regeneration. While in the regeneration vessel the catalyst is agitated and fluidized by the addition of a high temperature vapor phase stream comprising hydrogen and isobutane through line 10. This stream has been heated by means not shown to a sufficient temperature to cause the vaporization of at least a major portion of the liquid phase hydrocarbons which enter the regeneration vessel through line 8 in the second catalyst stream. There is thereby formed a vapor phase regeneration zone effluent stream comprising hydrogen, isobutane and any other hydrocarbons which enter the regeneration zone through line 8 or result from the regeneration process. This higher temperature hydrogen-rich stripping is a much more intense regeneration procedure and is preferably performed at conditions yielding a catalyst residence time of at least 30 minutes within the regeneration vessel 9.

A stream of fully regenerated catalyst is removed from the regeneration zone via line 12 at a rate controlled by slide valve 13. This rate is preferably approximately equal to the rate at which catalyst is fed into the regeneration zone but may fluctuate over short periods. The highly regenerated catalyst first flows through a catalyst cooler 14 which receives low temperature isobutane through line 15 and is then passed into the bottom of a second riser 17. The catalyst is preferably cooled to a temperature below about 38° C. A stream of liquid-phase isobutane from line 16 then fluidizes the highly regenerated catalyst and causes it to flow upward into the separation vessel 4 where it is commingled with the catalyst which has been subjected to the mild regeneration. It has been noted that highly regenerated catalyst tends to produce lower octane number product and the use of a blend of fresh and mildly regenerated used catalyst should reduce this tendency. As shown on the drawing, the catalyst from the transfer riser 17 preferably enters the separation vessel 4 in the upper half of the vessel 4 to avoid the pressure head of the catalyst retained in the vessel 4. Alternatively, the transfer riser 17 may direct the highly regenerated catalyst into the dense bed of catalyst present in the lower portion of the separation vessel. This may be done to increase the degree of fluidization at the bottom of the separation vessel. The highly regenerated catalyst could also be fed directly into the riser 2. The higher volume of mildly regenerated catalyst and its greater rate of circulation overwhelms the addition rate from line 17.

The circulation of the catalyst through the high temperature regeneration zone requires the catalyst to be heated and cooled. The utility requirements of the process also require that the heat of reaction of the alkylation reaction be removed. These activities can be integrated with the operation of the products recovery section of the process. For instance, the heat available in the vapor phase stream discharged via line 11 from the high temperature regeneration vessel 9 can be used to aid in reboiling a fractionation column. Heat can also be supplied to the product recovery section from the cooler 14 used to cool catalyst being returned to the riser-reactor. Alternatively, the heated coolant may be passed into the regeneration zone 9.

Figure 2:
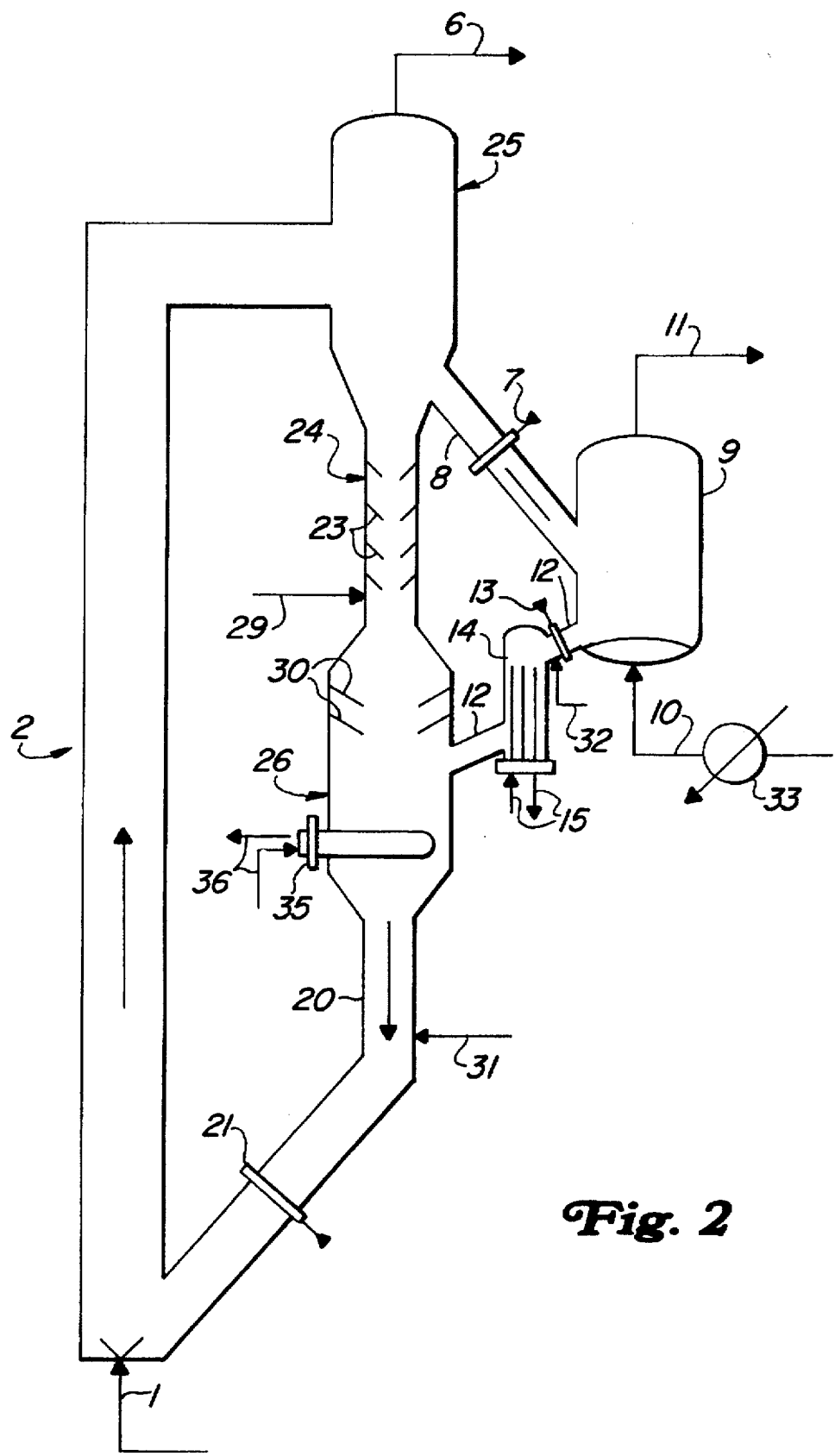
FIG. 2 illustrates a second embodiment of the invention in which the riser reactor discharges into a separation zone 25 and the majority of the used catalyst is then subjected to mild regeneration in a segregated washing section 24 located below the hydrocyclone.

FIG. 2 illustrates a different embodiment of the subject process. Like the embodiment of FIG. 1, the feed hydrocarbon and feed olefin reactants enter the bottom of a riser reactor 2 through line 1. Regenerated catalyst flowing downward through the transfer conduit 20 at a rate controlled by the slide valve 21 is admixed with the entering feed hydrocarbons and fluidized upward through the riser 2. At the upper terminal end of the riser 2, the olefin-free reactant-catalyst admixture is directed horizontally into a hydrocyclone 25 which functions as the separation zone. The hydrocyclone is the sole solids-liquid separation device employed in this embodiment. The residual feed hydrocarbon which has not been converted in the riser-reactor and the product hydrocarbons exit from the upper end of the hydrocyclone through line 6 for transfer to the product recovery zone. The used catalyst separated in this manner from the reactants passes downward through the lower portion of the hydrocyclone. A first small portion of this used catalyst is diverted from the bottom of the hydrocyclone through conduit 8 at a rate controlled by slide valve 7. This small portion of the used catalyst is passed directly into the high intensity external regeneration vessel 9. In comparison, the embodiment of FIG. 1 diverts catalyst which has been subjected to mild regeneration.

Regeneration vessel 9 is operated in a manner similar to the external regeneration zone of the embodiment of FIG. 1. The catalyst is preferably confined within this regeneration zone for an average residence time of at least 30 minutes while being contacted with a heated stream of hydrogen and isobutane fed to the bottom of the regeneration zone 9 through line 10. This hot hydrogen-hydrocarbon stripping removes liquid phase hydrocarbons and deposits from the catalyst and produces a vapor phase regeneration zone effluent stream removed from the regeneration zone 9 through line 11. This regeneration zone effluent stream is preferably cooled sufficiently to condense substantially all of the hydrocarbons contained within this stream and then subjected to vapor-liquid separation. The recovered liquids are passed into the products recovery zone and the hydrogen may be recycled to the bottom of the regeneration zone.

Catalyst which has been subjected to the high temperature stripping is withdrawn from vessel 9 through line 12 at a rate controlled by the slide valve 13. This hot catalyst is admixed with liquid phase isobutane from line 32 and then passed into the heat exchanger 14. Isobutane coolant supplied by line 15 is used to cool the catalyst to less than about 38° C. and the catalyst then flows into the stripping section 26. Catalyst cooling may be used to heat and/or vaporize the isobutane. Vaporization has some advantages.

The majority of the catalyst collected in the bottom of the hydrocyclone 25 passes downward through a liquid-filled wash section 24 which functions as the mild regeneration zone in this embodiment. The descending catalyst preferably passes through a series of funnel-shaped baffles 23 intended to admix and stir the catalyst and promote uniform contacting of the descending catalyst with a rising stream of hydrogen saturated isobutane injected into the bottom of the wash section through line 29. The countercurrent contacting within the wash zone 24 imparts a mild regeneration to the used catalyst descending from the hydrocyclone. The hydrogen saturated isobutane rises into the hydrocyclone and is removed with the product stream of line 6.

The mildly regenerated catalyst descending through the wash section enters the stripping section 26 where it is contacted with an additional quantity of upward flowing isobutane from line 31. The catalyst descends through the stripping zone 26 countercurrent to the rising hydrogen-free isobutane. A second series of inclined conical or funnel-like baffles 30 is provided in the stripping zone at various locations to ensure admixing of the rising isobutane with the descending catalyst and a thorough removal of hydrogen from the catalyst. Although the baffles 30 are shown only above the junction with the transfer conduit 12 they may be located below this point also. At the midpoint of the stripping section, the descending catalyst stream from the wash section is joined and admixed with the stream of highly regenerated catalyst removed from the external regeneration zone 9. Additional cooling is provided to the bottom of the stripping section 26 by means of indirect heat exchanger 35 located at the bottom of the stripping section which receives coolant through lines 36. This cooling results in the catalyst being brought to the desired reaction zone inlet temperature before passage into the riser 2. The upward flow of hydrogen-free isobutane from line 31 is relied upon to flush hydrogen from the catalyst stream of line 12.

The steps of the subject process include the regeneration of catalyst located in one regeneration zone by contact with a liquid-phase hydrocarbon, which is preferably the feed hydrocarbon such as isobutane. Hydrogen is preferably dissolved in this liquid-phase stream up to the point of the stream containing the stoichiometrically required amount of hydrogen. For purposes of this calculation, it is assumed that the carbonaceous material is composed of monoolefinic octenes, which allows for control of the hydrogen addition rate from an analysis of the catalyst. The average residence time of catalyst particles in the liquid-phase hydrocarbon regeneration zone is preferably from about 0.5 to 15 minutes. The liquid-phase or "mild" regeneration is performed in a vessel or conduit in relatively open communication with the reaction zone. The temperature and pressure conditions employed in this regeneration zone will therefore be very similar to those in the reaction zone. Further information on the regeneration of the subject catalyst may be obtained from U.S. patent application 08/043,954.

The subject process also includes a second regeneration operation in which catalyst is contacted with a vapor-phase gas stream at an elevated temperature in the range of about 80 to about 500 degrees C. and more preferably from 100° to 250° C. The zone in which this "hydrogen stripping" or severe regeneration step is performed is operated in a manner which provides a longer average residence time for the catalyst particles than the liquid-phase regeneration step. The average residence time of a catalyst particle should be at least 30 minutes and can reach about 12 to 24 hours. This regeneration step is performed using a vapor-phase hydrogen rich gas stream. The presence of some isobutane in this gas stream is desirable to increase the heat capacity of the gas and therefore increase catalyst heat up rates. The longer residence time required for this regeneration step allows the high temperature gas charged to the regeneration zone to vaporize liquid which flows into the severe regeneration zone.

All of the catalyst passing from the separation zone to the bottom of the riser is preferably subject to one of the two forms of regeneration. A much smaller quantity of catalyst flows through the hydrogen stripping regeneration zone compared to the flow through the liquid-phase regeneration. The flow through the high temperature regeneration zone will be only about 0.2 to about 20 weight percent, and preferably from about 0.4 to about 5 weight percent of the total catalyst flow through the riser.

The catalyst flow into the bottom of the riser is preferably as close to a continuous steady state flow as the equipment and catalyst system allow. The flow can, however, be in the form of numerous small quantities of catalyst transferred in rapid sequence.

The Drawing and above description are presented in terms of controlling catalyst flow through the use of slide valves. Alternative means can be used for this purpose including, for example, other types of valves, lockhoppers, fluid flow control (reverse flow of liquid), screw conveyors, etc. One particular alternative is the use of an "L valve", which would reduce the amount of isobutane flush needed in the process.

The embodiment shown in the Drawing may also be varied by the use of other types of heat exchangers and by the use of other coolants. While the use of isobutane as coolant and integration with the product fractionation zone is preferred, other coolants including water, air or other hydrocarbons can be employed. A further variation encompasses the use of countercurrent fluid flow to simultaneously cool newly regenerated catalyst and to flush hydrogen from the catalyst and liquid surrounding the catalyst.

The subject process can be performed using any solid, that is, heterogeneous, catalyst which is stable and has the required activity and selectivity for the desired reaction at the conditions needed to maintain liquid-phase reactants in the reaction zone. A large number of catalysts have been proposed for the production of motor fuel by alkylation including various zeolites and superacid catalysts. For instance, U.S. Pat. No. 4,384,161 describes the use of a large pore zeolite and a Lewis acid. The zeolites referred to include ZSM-4, ZSM-3, the faujasites including zeolite Y and mordenite. The Lewis acids mentioned in this reference include boron trifluoride and aluminum chloride. The alkylation of isoparaffins using a somewhat similar catalyst system comprising a large pore crystalline molecular sieve such as a pillared silicate or an aluminophosphate or silicoaluminophosphate together with a gaseous Lewis acid is disclosed in U.S. Pat. No. 4,935,577. The use of these Lewis acids is not preferred in the subject process as they provide their own waste handling and safety problems. They also will probably require provisions for the circulation of the Lewis acid, which may complicate the process as shown by the teaching of the just cited U.S. Pat. No. 4,935,577. U.S. Pat. No. 5,157,200 describes an isoparaffin alkylation process using a catalyst comprising a crystalline transition alumina, preferably eta or gamma alumina, which has been treated with a Lewis acid under anhydrous conditions. Previously referred to U.S. Pat. No. 5,157,196 describes an isoparaffin alkylation process using a slurried solid catalyst, with the preferred catalyst being an acid washed silica which has been treated with antimony pentafluoride. Both of these last two references describe a number of prior art solid bed paraffin alkylation catalysts.

A preferred paraffin alkylation catalyst comprises a refractory inorganic oxide impregnated with a monovalent cation, especially an alkali metal cation or an alkaline earth metal cation, and whose bound surface hydroxyl groups have been at least partially reacted with a Friedel-Crafts metal halide. Analogs of these catalysts without the metal cations are described in U.S. Pat. Nos. 2,999,074 and 3,318,820 which describe preparation techniques which can be applied to the preferred catalysts. The preferred refractory oxide is alumina having a surface area greater than 50 m²/g, but the use of other oxides including titania, zirconia, silica, boria and aluminum phosphate is contemplated. The preferred catalyst also contains a metal component active for olefin hydrogenation deposited on the inorganic oxide prior to reaction of the bound surface hydroxyl groups with the metal halides. This metal may be chosen from the group consisting of nickel, platinum, palladium, and ruthenium with the first three of these metals being preferred. The catalyst contains one or more monovalent metal or alkaline earth metal cations selected from the group consisting of lithium, sodium, potassium, cesium, silver, copper, beryllium, magnesium, calcium and barium. Subsequent to the deposition of these metals and the controlled calcination of the composite, the composite is reacted with a Friedel-Crafts metal halide. The metal may be aluminum, zirconium, tin, tantalum, gallium, antimony or boron. Suitable halides are the fluorides, chlorides and bromides. This preferred catalyst has been found to be sensitive to low levels of water as may be generated from oxygenates in the feed streams. Very low levels of such oxygenates as butanols are therefore important to catalyst life and successful process operation.

The presence of a highly active metal hydrogenation component on the catalyst will promote hydrogenation of the feed olefin if both the olefin and hydrogen simultaneously contact the catalyst. This potential waste of the olefin and hydrogen can be avoided by careful design and operation of the process to avoid having both the olefin and hydrogen in simultaneous contact with the catalyst. This can be done by flushing the hydrogen or olefin from the catalyst before inserting it into a zone containing the other compound as described above.

Silicalites have been described as useful alkylation catalysts for the production of monoalkylbenzenes in U.S. Pat. No. 4,489,214 to J. R. Butler et al. and as useful in methylating toluene to produce paraxylene in U.S. Pat. No. 4,444,989 issued to F. E. Herkes. The use of ZSM-5 zeolites in aromatic alkylation is described in U.S. Pat. No. 3,751,506. ZSM-5 zeolites that have been treated with one or more compounds or elements to improve their selectivity for para-selective alkylation of aromatic hydrocarbons are described in U.S. Pat. No. 4,420,418. The use of zeolite L, zeolite Omega and zeolite beta as alkylation catalysts for the selective alkylation of benzene is described in U.S. Pat. No. 4,301,316. The use of a number of natural and synthetic zeolites including clinoptilolite and zeolite Y as alkylation catalysts is described in U.S. Pat. No. 3,251,897.

The catalyst may be in the form of any suitable shape and size which results in a solid catalyst which flows readily in both dry and wet states and which is readily fluidized at the moderate liquid flow rates employed in the riser. The catalyst can therefore be present as small irregular particles or as uniformly shaped particles. It is preferred that the catalyst is present as "microspheres" having an average diameter less than about 0.16 cm and more preferably less than about 0.08 cm.

Operating temperature is measured at the outlet of the reaction zone, with the temperatures specified herein based upon an assumed temperature rise of 20–50 degrees F. in the riser. Suitable operating conditions for the reaction zone include a temperature measured at the reactor outlet of about –17 to 77 degrees C., preferably 10 to 38 degrees C., and a pressure as required to maintain the hydrocarbons present as a liquid. An elevated pressure above that required to maintain liquid phase conditions has been found to favorably increase the apparent activity of the preferred catalyst and is therefore beneficial. However, with portions of the plant having vapor phase conditions, a moderate pressure in the general range of about 120 to about 3500 kPa is preferred with 2000–3000 kPa being highly preferred. The catalyst to olefin ratio (weight) in the reaction zone can be within the broad range of about 1:1 to about 1:25 and is preferably between 3:1 and 15:1. The residence times of the catalyst and the hydrocarbon phase will be quite similar and can vary within the broad range of 5 seconds to 20 minutes. The riser reaction zone is preferably designed and operated in a manner intended to promote plug flow (no backmixing) of the reactants, products and catalyst within the riser. However, the liquid must flow upward faster than the catalyst in order to transport it.

It is generally preferred that the reaction zone is operated with an excess of the feed hydrocarbon compared to the alkylating agent. That is, it is preferred to operate with a ratio of the feed paraffinic or aromatic hydrocarbon to a feed olefin at the reactor entrance greater than 1:1, and preferably from about 2:1 to about 5:1 or higher as measured by the flow rates into the reaction zone. It is highly preferred to operate with an abundance of isoparaffin compared to alkylating agent in a motor fuel alkylation process. Specifically, it is preferred that the molar ratio of isoparaffin to olefin being charged to the reaction zone is greater than 2:1 and more preferably greater than 3:1. Ratios from 10:1 to about 100:1 or higher can be employed for motor fuel alkylation. The known technique of feeding the olefin at a number of points along the flow path of the feed hydrocarbon may be employed to maintain a higher average paraffin to olefin ratio.

Provisions may be made for removing used catalyst from the reaction zone and to replace the used catalyst with fresh catalyst. Conventional valved lockhopper systems may be used for this purpose.

One preferred embodiment of the invention may accordingly be characterized as a process for the alkylation of a feed hydrocarbon which comprises the steps of passing a first catalyst stream, comprising regenerated catalyst, and a feed stream comprising the feed hydrocarbon and an alkylating agent into the bottom of a vertical riser-reaction zone maintained at reaction conditions and producing a reaction zone effluent stream comprising used catalyst, the feed hydrocarbon and a product hydrocarbon; discharging the reaction zone effluent stream into a separation zone in which used catalyst is separated from the liquid phase product hydrocarbon and thereby forming a liquid-phase separation zone effluent stream comprising the feed and product hydrocarbons, with the thus separated used catalyst descending downward within the separation zone; transferring a major first portion of the used catalyst downward through a mild regeneration zone wherein the used catalyst is countercurrently contacted with feed hydrocarbon containing dissolved hydrogen and withdrawing catalyst from the mild regeneration zone as a second catalyst stream; transferring the remaining second portion of the used catalyst downward from the separation zone into a high temperature regeneration zone wherein the used catalyst is contacted with vapor phase hydrogen at vapor phase regeneration conditions and withdrawing catalyst from the high temperature regeneration zone as a third catalyst stream; commingling the second and third catalyst streams to form the first stream of catalyst; countercurrently contacting the first stream of catalyst with the feed hydrocarbon to remove hydrogen from the catalyst; and, recovering the product hydrocarbon from the separation zone effluent stream.

The subject invention may also be characterized as a motor fuel alkylation process for the solid catalyst alkylation of a paraffinic feed hydrocarbon which comprises the steps: passing a first catalyst stream, comprising regenerated catalyst, and a feed stream comprising the $C_4$ paraffinic feed hydrocarbon and a $C_4$ olefinic hydrocarbon into the bottom of a vertical riser-reaction zone maintained at reaction conditions and producing a reaction zone effluent stream comprising used catalyst, the feed hydrocarbon and a product hydrocarbon; discharging the reaction zone effluent stream into a separation zone in which used catalyst is separated from the liquid phase product hydrocarbon and thereby forming a liquid-phase separation zone effluent stream comprising the feed and product hydrocarbons, with the thus separated used catalyst descending downward within the separation zone; transferring the used catalyst downward through a mild regeneration zone located in the same vessel as the separation zone and wherein the used catalyst is countercurrently contacted with the feed hydrocarbon containing dissolved hydrogen and withdrawing catalyst from the mild regeneration zone as a second catalyst stream; countercurrently contacting the second stream of catalyst with the feed hydrocarbon to remove hydrogen and hydrogen-containing liquid-phase hydrocarbons from the catalyst and thereby forming said first catalyst stream; transferring a portion of the used catalyst downward from the mild regeneration zone into a high temperature regeneration zone wherein the used catalyst is contacted with vapor phase hydrogen and the feed hydrocarbon at vapor phase regeneration conditions and withdrawing catalyst from the high temperature regeneration zone as a second catalyst stream; passing the second catalyst stream into the separation zone; and, recovering the product hydrocarbon from the separation zone effluent stream.

What is claimed:

1. A process for the alkylation of a feed hydrocarbon which comprises the steps:
   a. passing a first catalyst stream, comprising regenerated catalyst, and a feed stream comprising the feed hydrocarbon and an alkylating agent into the bottom of a vertical riser-reaction zone maintained at reaction conditions and producing a reaction zone effluent stream comprising used catalyst, the feed hydrocarbon and a product hydrocarbon;
   b. discharging the reaction zone effluent stream into a separation zone in which used catalyst is separated from liquid phase hydrocarbons and thereby forming a liquid-phase separation zone effluent stream comprising the feed and product hydrocarbons, with the thus separated used catalyst descending downward within the separation zone;
   c. transferring the used catalyst downward through a mild regeneration zone wherein the used catalyst is contacted with feed hydrocarbon containing dissolved hydrogen to form partially regenerated catalyst;
   d. transferring a portion of the used catalyst into a high temperature regeneration zone wherein the used catalyst is contacted with vapor phase hydrogen at vapor phase regeneration conditions to form regenerated catalyst, and withdrawing regenerated catalyst from the high temperature regeneration zone as a second catalyst stream;
   e. commingling the second catalyst stream with partially regenerated catalyst and employing at least a portion of the resulting admixture as the first stream of catalyst, which is admixed with the feed stream as per step (a); and,
   f. recovering the product hydrocarbon from the separation zone effluent stream.

2. The process of claim 1 further characterized in that the catalyst is spherical.

3. The process of claim 1 further characterized in that the feed hydrocarbon is an aromatic hydrocarbon.

4. The process of claim 1 further characterized in that the feed hydrocarbon is an paraffinic hydrocarbon.

5. The process of claim 1 further characterized in that the alkylating agent is an olefinic hydrocarbon.

6. A process for the alkylation of a feed hydrocarbon which comprises the steps:
   a. passing a first catalyst stream, comprising regenerated catalyst, and a feed stream comprising the feed hydrocarbon and an alkylating agent into the bottom of a vertical riser-reaction zone maintained at reaction conditions and producing a reaction zone effluent stream comprising used catalyst, the feed hydrocarbon and a product hydrocarbon;
   b. discharging the reaction zone effluent stream into a separation zone in which used catalyst is separated from the liquid phase product hydrocarbon and thereby forming a liquid-phase separation zone effluent stream comprising the feed and product hydrocarbons, with the thus separated used catalyst descending downward within the separation zone to form a dense bed of catalyst retained in a lower portion of the separation zone and in which the used catalyst is subjected to a mild regeneration by contact with the feed hydrocarbon containing dissolved hydrogen to form partially regenerated catalyst;
   c. transferring a second catalyst stream, comprising the partially regenerated catalyst, from said dense bed of catalyst through a transfer conduit wherein the partially regenerated catalyst is contacted with the feed hydrocarbon to remove hydrogen and thereby forming said first catalyst stream;
   d. transferring catalyst from said dense bed of catalyst into a high temperature regeneration zone wherein the catalyst is contacted with vapor phase hydrogen at vapor-phase regeneration conditions to form regenerated catalyst and withdrawing regenerated catalyst from the high temperature regeneration zone as a third catalyst stream;
   e. commingling the regenerated and partially regenerated catalyst; and
   f. recovering the product hydrocarbon from the separation zone effluent stream.

7. The process of claim 6 further characterized in that the feed hydrocarbon is an aromatic hydrocarbon.

8. The process of claim 6 further characterized in that the feed hydrocarbon is an paraffinic hydrocarbon.

9. The process of claim 6 further characterized in that the alkylating agent is an olefinic hydrocarbon.

10. A motor fuel alkylation process for the solid catalyst alkylation of a paraffinic feed hydrocarbon which comprises the steps:

a. passing a first catalyst stream, comprising regenerated catalyst, and a feed stream comprising the $C_4$ paraffinic feed hydrocarbon and a $C_4$ olefinic hydrocarbon into the bottom of a vertical riser-reaction zone maintained at reaction conditions and producing a reaction zone effluent stream comprising used catalyst, the feed hydrocarbon and a product hydrocarbon;

b. discharging the reaction zone effluent stream into a separation zone in which used catalyst is separated from the liquid phase product hydrocarbon and thereby forming a liquid-phase separation zone effluent stream comprising the feed and product hydrocarbons, with the thus separated used catalyst descending downward within the separation zone;

c. transferring the used catalyst downward through a mild regeneration zone located in the same vessel as the separation zone and wherein the used catalyst is countercurrently contacted with the feed hydrocarbon containing dissolved hydrogen, and withdrawing catalyst from the mild regeneration zone as a second catalyst stream;

d. countercurrently contacting the second stream of catalyst with the feed hydrocarbon to remove hydrogen and hydrogen-containing liquid-phase hydrocarbons from the catalyst and thereby forming said first catalyst stream;

e. transferring a portion of the used catalyst from the mild regeneration zone into a high temperature regeneration zone wherein the used catalyst is contacted with vapor phase hydrogen and the feed hydrocarbon at vapor phase regeneration conditions and withdrawing catalyst from the high temperature regeneration zone as a second catalyst stream;

f. passing the second catalyst stream into the separation zone; and, g. recovering the product hydrocarbon from the separation zone effluent stream.

* * * * *